United States Patent
Kelada et al.

(10) Patent No.: US 11,246,815 B2
(45) Date of Patent: Feb. 15, 2022

(54) GENTLE CLEANSER COMPOSITIONS

(71) Applicant: L'OREAL, Paris (FR)

(72) Inventors: Meriam Kelada, Bloomfield, NJ (US); Carol Ragai Elmasry, South Amboy, NJ (US); Gregory Shmuylovich, Springfield, NJ (US)

(73) Assignee: L'OREAL, Paris (FR)

( * ) Notice: Subject to any disclaimer, the term of this patent is extended or adjusted under 35 U.S.C. 154(b) by 105 days.

(21) Appl. No.: 15/966,087

(22) Filed: Apr. 30, 2018

(65) Prior Publication Data

US 2019/0328641 A1 Oct. 31, 2019

(51) Int. Cl.
| | | |
|---|---|---|
| C11D 1/90 | (2006.01) | |
| C11D 1/94 | (2006.01) | |
| C11D 3/20 | (2006.01) | |
| A61K 8/46 | (2006.01) | |
| A61K 8/26 | (2006.01) | |
| A61K 8/365 | (2006.01) | |
| A61K 8/37 | (2006.01) | |
| A61K 8/44 | (2006.01) | |
| A61Q 19/10 | (2006.01) | |
| C11D 3/12 | (2006.01) | |
| C11D 3/37 | (2006.01) | |
| C11D 1/14 | (2006.01) | |

(52) U.S. Cl.
CPC .......... *A61K 8/466* (2013.01); *A61K 8/26* (2013.01); *A61K 8/365* (2013.01); *A61K 8/37* (2013.01); *A61K 8/442* (2013.01); *A61Q 19/10* (2013.01); *C11D 1/143* (2013.01); *C11D 1/90* (2013.01); *C11D 1/94* (2013.01); *C11D 3/1253* (2013.01); *C11D 3/2093* (2013.01); *C11D 3/3757* (2013.01)

(58) Field of Classification Search
CPC .. C11D 1/143; C11D 1/90; C11D 1/94; C11D 3/1253; C11D 3/2093; C11D 3/3757
USPC ....... 510/123, 127, 130, 136, 137, 138, 475, 510/488, 507
See application file for complete search history.

(56) References Cited

U.S. PATENT DOCUMENTS

| | | | |
|---|---|---|---|
| 4,800,197 A | 1/1989 | Kowcz | |
| 5,569,651 A | 10/1996 | Garrison | |
| 2002/0183217 A1* | 12/2002 | Perron | A61K 8/375 510/130 |
| 2005/0101499 A9* | 5/2005 | Lazzeri | A61K 8/442 510/130 |
| 2006/0127458 A1 | 6/2006 | Kiser et al. | |
| 2009/0062406 A1 | 3/2009 | Loeffler | |
| 2012/0021025 A1* | 1/2012 | Bendejacq | A61K 8/0295 424/401 |
| 2012/0093748 A1* | 4/2012 | Fares | A61K 8/365 424/62 |
| 2013/0336905 A1* | 12/2013 | Fares | A61K 8/37 424/59 |
| 2015/0005266 A1* | 1/2015 | Purcell | A61K 31/07 514/163 |
| 2017/0100314 A1* | 4/2017 | Diekhof | A61K 8/062 |
| 2017/0172886 A1* | 6/2017 | Osborne | A61K 8/046 |
| 2017/0304173 A1 | 10/2017 | Elder et al. | |
| 2018/0326194 A1* | 11/2018 | Rodan | A61B 17/3205 |

FOREIGN PATENT DOCUMENTS

| | | |
|---|---|---|
| WO | 9747171 A1 | 12/1997 |
| WO | 2013159865 A1 | 10/2013 |
| WO | 2015179599 A1 | 11/2015 |
| WO | 15181789 A1 | 12/2015 |
| WO | 2017140799 A1 | 8/2017 |

OTHER PUBLICATIONS

International Search Report and Written Opinion in corresponding PCT application PCT/US2019/026890, dated Nov. 7, 2019, 12 pages.

* cited by examiner

*Primary Examiner* — Gregory R Delcotto
(74) *Attorney, Agent, or Firm* — Laetitia Leproust; Runzhi Zhao

(57) ABSTRACT

The present disclosure relates to gentle cleanser compositions, which generally include: (a) a taurate surfactant; (b) salicylic acid; (c) kaolin; d) a betaine (and/or another amphoteric surfactant) and e) an emollient. The cleanser compositions exhibit very good cleansing properties, are particularly effective for removing makeup, and are mild and moisturizing to the skin, with a good deposition of salicylic acid.

15 Claims, No Drawings

GENTLE CLEANSER COMPOSITIONS

FIELD OF THE DISCLOSURE

The present disclosure relates to gentle cleanser compositions. The cleanser compositions exhibit very good cleansing properties, are particularly effective for removing makeup, are mild, moisturizing to the skin and help the deposition of salicylic acid.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem in low-surfactant formulations, as foam volume tends to decrease with decreasing surfactant concentration.

Sulfate-based surfactants (such as, for example, sodium lauryl sulfate and sodium lauryl ether sulfate) are particularly popular because of their effectiveness in cleansing, foam production, and stability. Personal care cleansers containing sulfate-based surfactants are also generally easy to thicken with typical thickeners, such as salt and cellulose-based materials. Nonetheless, these particular surfactants can be harsh and irritating to skin. For instance, over-use of sulfate-based surfactants can cause needless drying to the face and scalp, and contribute to color fading and drying of hair. Eliminating sulfate surfactants from cleansing compositions has been challenging because sulfate-free compositions typically have poor foaming properties, are difficult to thicken, are not clear (not transparent). Also, the cleansing ability of sulfate-free composition are often sub-optimal.

SUMMARY OF THE DISCLOSURE

The cleanser compositions of the instant disclosure are surprisingly effective yet mild and moisturizing to the skin as well as effective for acne prone skin. The cleanser compositions are particularly unique in that they are gentle, provide a "clean" and refreshing feel during use, and are surprisingly effective at removing make-up from the skin. Finally, the cleanser compositions are very stable, which is important for providing a long-lasting and durable product for consumers.

The instant disclosure relates to a cleanser composition comprising:
a) from about 0.5% to about 20% of a taurate surfactant;
b) from about 0.5% to about 2% of salicylic acid;
c) from about 0.8% to about 40% of kaolin;
d) from about 1% to about 15% of a betain; and
e) from about 0.5% to about 5% of an emollient;
wherein all amounts are percentages by weight based on the total weight of the composition;
wherein the composition is essentially free of sulfates.

In some cases, the taurate surfactant can be, for example, a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate. In some embodiments, the taurate surfactant is sodium methyl cocoyl taurate.

In one or more embodiments, the salicylic acid is from about 0.8% to about 2% by weight based on the total weight of the composition.

In one or more embodiments, the kaolin is from about 1% to about 30% of kaolin by weight based on the total weight of the composition. In one embodiment, the kaolin is from about 1.5% to about 20% of kaolin by weight based on the total weight of the composition.

In some cases, the betaine can be, for example, the betain selected from the group consisting of coco betaine, cocoamidopropyl betaine, lauryl betaine, laurylhydroxy sulfobetaine, lauryldimethyl betaine, cocoamidopropylhydroxylsulfo betaine, behenyl betaine, capryl/capramidopropyl betaine, lauryl hydroxysultaine, and stearyl betaine. In one embodiment, the betaine is coco betaine.

In some cases, the emollient can be, for example, a compound selected from the group consisting of C12-15 alkyl lactate, C12-13 alkyl lactate and mixtures thereof. In some embodiments, the emollient is C12-15 alkyl lactate.

In addition to the components described above, the cleanser compositions can additionally include: f) a rheology modifier (or a thickener). In one or more embodiments, the rheology modifier is ammonium polyacryloyldimethyl taurate.

Another aspect of the instant disclosure can include a cleanser composition comprising:
a) from about 1.5% to about 15% of a taurate surfactant;
b) from about 0.5% to about 2% of salicylic acid;
c) from about 0.8% to about 40% of kaolin;
d) from about 3% to about 10% of a betain;
e) from about 0.5% to about 5% of an emollient selected from the group of group consisting of C12-15 alkyl lactate, C12-13 alkyl lactate and mixtures thereof.
f) from about 0.5% to about 2.5% of polymer selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer; and
wherein all amounts are percentages by weight based on the total weight of the composition;
wherein the composition is essentially free of sulfates.

The cleanser compositions disclosed herein are particularly useful for cleansing the body, especially the skin. Additionally, the cleanser compositions disclosed herein are useful in methods for removing makeup from the skin. When cleansing and/or removing makeup such as foundation, blush, mascara, eye shadow from the skin, the compositions may be applied to the skin and rinsed from the skin with water. As mentioned above, the cleanser compositions are gentle to the skin and are also unique in their ability to hydrate the skin and to have a good deposition of salicylic acid. Therefore, the compositions may be used in methods for gently hydrating the skin during cleansing and help skin with acne problems.

DETAILED DESCRIPTION OF THE DISCLOSURE

The cleanser compositions of the instant disclosure, in their broadest sense, typically include the following:
a) from about 0.5% to about 20% of a taurate surfactant;
b) from about 0.5% to about 2% of salicylic acid;
c) from about 0.8% to about 40% of kaolin;
d) from about 1% to about 15% of a betain; and
e) from about 0.5% to about 5% of an emollient;
wherein all amounts are percentages by weight based on the total weight of the composition;
wherein the composition is essentially free of sulfates.

Without being bound by theory, it is believed that the kaolin participates in the deposition of the salicylic acid on the skin. Additionally, without wishing to be bound by theory, it is believed that the deposition of the salicylic acid helps oily skin and/or acne.

Taurate Surfactants

The taurate surfactants include those of Formula I, below:

$$R^7-\overset{O}{\underset{\|}{C}}-\underset{R^8}{\overset{|}{N}}-\underset{R^{10}}{\overset{R^9}{\underset{|}{CH}}}-CH-SO_3^- \quad M^+ \quad (I)$$

wherein,
$R^7$ is $(C_8-C_{22})$alkyl;
$R^8$ is H or $(C_1-C_4)$alkyl;
$R^9$ and $R^{10}$ are each independently H or $(C_1-C_4)$alkyl; and
$M+$ is a sodium, potassium, or ammonium cation.

In some embodiments, the taurate surfactant may be, for example, a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate. Likewise, in some instances, the taurate surfactant is sodium methyl cocoyl taurate.

The taurate surfactant may be present in an amount from about 0.5%, 1%, 1.5%, 2%, 2.2%, 2.4%, 2.5%, 2.6%, 2.8%, 3%, 3.2%, 3.4%, 3.5%, 3.6%, 3.8%, 4%, 4.2%, 4.4%, 4.5%, 4.6%, 4.8%, 5%, 5.2%, 5.4%, 5.5%, 5.6%, 5.8%, 6%, 6.2%, 6.4%, 6.5%, 6.6%, 6.8%, 7%, 7.2%, 7.4%, 7.5%, 7.6%, 7.8%, 8%, 8.2%, 8.4%, 8.5%, 8.6%, 8.8%, 9% to about 9%, 9.2%, 9.4%, 9.5%, 9.6%, 9.8%, 10%, 10.2%, 10.4%, 10.5%, 11%, 11.2%, 11.4%, 11.5%, 11.6%, 11.8%, 12%, 12.2%, 12.4%, 12.5%, 12.6%, 12.8%, 13%, 13.5%, 14%, 14.5%, 15%, 15.5%, 16%, 16.5%, 17%, 17.5%, 18%, 18.5%, or to 20%, by weight relative to the total weight of the composition.

Salicylic Acid

Salicylic acid, or 2-hydroxybenzoic acid, is provided to the cleanser composition to help the skin with acne problems. Salicylic acids is an effective keratolytic and comedolytic agent, inducing desquamation and can be used to effectively treat excessive oil, acne, post-inflammatory hyperpigmentation, and photodamage.

In some embodiments, the salicylic acid is from about 0.5%, 0.6%, 0.7%, 0.8%, 0.9%, 1% to about 1%, 1.1%, 1.2%, 1.3%, 1.4%, 1.5%, 1.6%, 1.7%, 1.8%, 1.9% or 2% by weight based on the total weight of the composition.

Clay

Clays are well-known products which are described, for example, in the publication Mineralogie des argiles [Mineralogy of Clays], S. Caillere, S. Henin and M. Rautureau, 2nd Edition, 1982, Masson.

Kaolin

Kaolin is a natural clay composed mainly of kaolinite, an aluminum silicate hydrate belonging to the phyllosilicate family.

A composition according to the invention may comprise a kaolin content ranging from 0.2%, 0.4%, 0.6%, 0.8%, 1%, 1.2%, 1.4%, 1.6%, 1.8%, 2%, 2.5%, 3%, 3.5%, 4%, 4.5%, 5%, 6%, 7%, 8%, 9%, 10%, 11%, 12%, 13%, 14%, 15%, 16%, 18%, 20%, 22%, 24%, 25% to about 25%, 26%, 27%, 28%, 29%, 30%, 31%, 32%, 33%, 35% or 40%, by weight relative to the total weight of the composition.

As kaolin that may be suitable for the present invention, mention may in particular be made of Kaolin supreme sold by Imerys or Coslin C 100 sold by BASF, preferably Kaolin supreme sold by Imerys.

Amphoteric Surfactant

The at least one amphoteric surfactant useful in the cosmetic compositions disclosed herein is chosen from betaines, sultaines, amphoacetates, amphoprionates, and mixtures thereof. More typically, betaines and amphoprionates are used, and most typically betaines. Betaines which can be used in the current compositions include those having the formulas (XXIIA-D) below:

$$R_{10}-\overset{CH_3}{\underset{|}{\underset{CH_3}{\overset{|}{N^+}}}}-(CH_2)_n-COO^- \quad (XXII\ A-B)$$

$$R_{10}-\overset{O}{\underset{\|}{C}}-\underset{H}{\overset{|}{N}}-CH_2-CH_2-\underset{H}{\overset{CH_2-CH_2-OH}{\underset{|}{N^+}}}-CH_2COO^-$$

$$R_{10}-\overset{CH_3}{\underset{|}{\underset{CH_3}{\overset{|}{N^+}}}}-(CH_2)_n-SO_3^- \quad (XXII\ C)$$

$$R_{10}-\overset{O}{\underset{\|}{C}}-\underset{H}{\overset{|}{N}}-(CH_2)_n-\underset{CH}{\overset{CH_3}{\underset{|}{N^+}}}-CH_2COO^- \quad (XXII\ D)$$

Wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

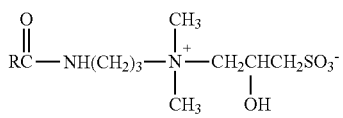
(XXIII)

wherein
R is an alkyl group having 8-18 carbon atoms.
Useful alkylamphoacetates include those having the formula (XXIV)

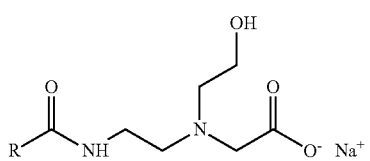
(XXIV)

wherein
R is an alkyl group having 8-18 carbon atoms.
useful alkyl amphodiacetates include those having the formula (XXV)

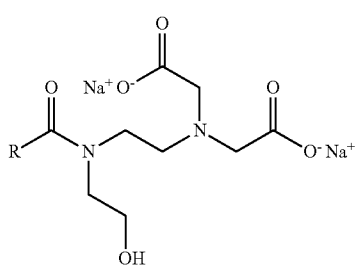
(XXV)

Wherein
R is an alkyl group having 8-18 carbon atoms.

In addition to the components described above, the cleanser compositions can include (d) a betaine and/or another amphoteric surfactant. Non-limiting examples of amphoteric surfactants include, in addition to betaines, sultaines, amphoacetates, and amphoproprionates. In some cases, when the amphoteric surfactant is a betaine, suitable betaines include coco betaine, cocoamidopropyl betaine, lauryl betaine, laurylhydroxy sulfobetaine, lauryldimethyl betaine, cocoamidopropylhydroxylsulfo betaine, behenyl betaine, capryl/capramidopropyl betaine, lauryl hydroxysultaine, and stearyl betaine. Finally, there are instances where the amphoteric surfactant is coco betaine.

The betaine and/or another amphoteric surfactant may be present in an amount from about 1%, 1.5%, 2%, 2.5%, 3%, 3.5%, 4%, 4.5%, 5%, 5.5%, 6%, 6.5%, 7%, 7.5%, 8%, 8.5%, 9%, 10% to about 10%, 10.5%, 11%, 11.5%, 12%, 12.5%, 13%, 13.5%, 14%, 14.5%, 15% by weight relative to the total weight of the composition.

Emollient
In some cases, the emollient can be, for example, a compound selected from the group consisting of C12-15 alkyl lactate, C12-13 alkyl lactate and mixtures thereof. In some embodiments, the emollient is C12-15 alkyl lactate, also known as Propanoic acid, 2-hydroxy-, C12-15-alkyl esters.

The emollient may be present in an amount from about 0.5%, 0.6%, 0.8%, 1%, 1.1%, 1.2%, 1.3%, 1.4%, 1.5%, 1.6%, 1.7% to about 1.7%, 1.8%, 1.9%, 2%, 2.4%, 2.6%, 2.8%, 3%, 3.5%, 4%, 4.5%, or 5% by weight based on the total weight of the composition.

Rheology Modifier/Thickener
The rheology modifier may be present in an amount of 0.01%, 0.05%, 1%, 1.2%, 1.3%, 1.4%, 1.5%, 1.6%, 1.7%, 1.8%, 1.9%, 2%, 2.2% to 2.2%, 2.3%, 2.4%, 2.5%, 2.6%, 2.8%, 3%, 3.2%, 3.4%, 3.6%, 3.8%, 4%, 4.5% or 5%, by weight based on the total weight of the composition.

Consumers expect of their cleansing products have an aesthetically pleasing viscosity. Formulations that flow with a watery consistency are aesthetically unpopular to consumers with expectations of rich and creamy products. While low viscosity products may be effective for their intended purpose, they are perceived to be of low quality by the consumer. Formulations that flow with a watery consistency run off when applied.

They are many known rheology modifiers. For example, the rheology modifier can be selected from the group consisting of: a polysaccharide; homopolymers of acrylic acid; acrylic acid cross-linked with a polyfunctional compound; hydrophobically-modified copolymers of acrylic acid, acrylate esters, maleic acid and the like; polyethylene glycol units of varying length connected by urethane linkages and terminated with hydrophobic end groups; organoclays; silicas; and fatty alcohols.

Rheology modifiers are used in aqueous cleansing products to manipulate the viscosity, usually to increase the viscosity to make them easier for the user to handle and/or to increase the yield stress of the composition. While a certain rheology modifiers may thicken or enhance the viscosity of a composition in which it is included, it may not necessarily have desirable yield stress properties. A desirable yield stress property is critical to achieving certain physical and aesthetic characteristics in a liquid medium, such as overall formula stability. An acceptable yield stress value can impart a formula with adequate shelf life stability. It can also help suspend particles, insoluble liquid droplets, or gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. A yield stress fluid is used generally to adjust or modify the rheological properties of aqueous compositions. Such properties include, without limitation, viscosity improvement, flow rate improvement, stability to viscosity change over time, and the ability to suspend particles for indefinite periods of time.

The rheology modifier may be xanthan gum, guar gum, biosaccharide gum, cellulose, acacia Seneca gum, sclerotium gum, agarose, pechtin, gellan gum, hyaluronic acid. Additionally, the rheology modifier may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from B.F. Goodrich (e.g., Carbopol® 954). In addition, other suitable carboxylic acid polymeric agents include Carbopol Ultrez® 20 (Lubrizol Corp.), which is acrylates/C10-C30 alkyl acrylate crosspolymer, Ultrez® 10 (B.F. Goodrich), and copolymers of C10-C30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. An exemplary polyacrylamide polymers is, for example, ammonium polyacryloyldimethyl taurate (Clariant Hostacerin AMPS).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Gums and Polysaccharides

A wide variety of gums and polysaccharides can be useful herein as gelling agents. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Further polysaccharides include starch derivatives (for example, starch oxide, dialdehyde starch, dextrin, British gum, acetyl starch, starch phosphate, carboxymethyl starch, hydroxyethyl starch, hydroxypropyl starch).

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Other thickening and gelling agents useful herein include materials which are primarily derived from natural sources. Nonlimiting examples of these gelling agents are gums such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

The cleanser composition described herein may be free or essentially free of one, two, three, or all of sulfates, soaps, fatty alcohols, and/or nonionic surfactants. In some cases, the cleanser compositions are soap free and sulfate free. Alternatively, each of these components may independently and individually (or in combination) be present in amounts less than 5 wt. %, 4 wt. %, 3 wt. %, 2 wt. %, 1 wt. %, 0.5 wt. %, 0.1 wt. %, 0.05 wt. %, or 0.01 wt. %. For example, in some cases, the cleanser compositions are essentially free of sulfates, but include less than the amounts set forth above of nonionic surfactants. Alternatively, the cleanser compositions may comprise less than 2 wt. % of nonionic surfactants and less than 0.5 wt. % of fatty alcohols. Additionally, the cleanser composition may have less than 4 wt. % of a combination of sulfates, soaps, fatty alcohols, and nonionic surfactants.

The cleanser composition may be in the form of an emulsion, e.g., oil-in-water (O/W), water-in-oil (W/O), and oil-in-alcohol emulsions, although the cleanser compositions are often not in the form of an emulsion. The compositions of the instant disclosure may be in the form of a liquid emulsion, such as a liquid-lotion, liquid-gel, liquid-cream, or a cream emulsion, such as a thick cream or gel-cream, or a foam or mousse wherein the liquid emulsion form has a thinner consistency than the cream emulsion form.

The cleanser compositions disclosed herein are particularly useful in methods for cleansing the body, especially the skin, and particularly the skin of the face, wherein the methods comprise applying a composition disclosed herein to the body, skin, and/or face, and rinsing the cleanser composition or wiping-away the composition from the face. Additionally, the cleanser compositions disclosed herein are useful in methods for removing makeup from the skin, especially the skin of the face. The makeup can be in the form of a foundation, blush, lipstick, gloss, mascara, and eye shadow. The compositions may be applied to the skin and removed from the skin by rinsing. Finally, the compositions may be used in methods for gently hydrating the skin comprising application of the composition to the skin as well improving the deposition of salicylic acid.

More exhaustive but non-limiting lists of components useful in the hair care compositions disclosed herein are presented below.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

The following Examples are provided for illustrative purposes only, and are not intended to be limiting.

Example 1: Inventive Example and Comparative Examples

TABLE 1

| | | Cleanser Compositions | | | | | |
|---|---|---|---|---|---|---|---|
| Claim component | INCI US NAME | Inventive Example 1 | Inventive Example 2 | Comparative Example 1 | Comparative Example 2 | Comparative Example 3 | Comparative Example 4 |
| (a) | Sodium Methyl Cocoyl Taurate | 3 | 3 | 3 | 3 | 3 | 3 |
| (e) | C12-15 alkyl lactate | 1.2 | 1.2 | 1.2 | 1.2 | 1.2 | 1.2 |
| (d) | Coco-Betaine | 5.4 | 5.4 | 5.4 | 5.4 | 5.4 | 5.4 |
| (b) | Salicylic Acid | 2 | 2 | 2 | 2 | 2 | 2 |
| (c) | Kaolin | 2 | 2 | 0 | 10 | 20 | 30 |
| (f) | Rheology Modifier | 1.5 | 1.5 | 1.5 | 1.5 | 1.5 | 1.5 |
| | Propylene glycol (and) PEG-55 Propylene Glycol Oleate | | 0.1 | | | | |
| | Preservatives, pH adjuster, co-solvents, polymers, fillers and fragrances | 1-5 | 1-5 | 1-5 | 1-5 | 1-5 | 1-5 |
| | Water | Q.S | Q.S. | Q.S | Q.S | Q.S | Q.S |

The Inventive and Comparative Examples in Table 1 were prepared according to the procedure as follows: the main kettle was heated to 70 C. Once the temperature was reached, 90% of water was added to the main kettle, as well as preservatives, solvent, salicylic acid, pH adjuster, emulsifier, and C12-15 alkyl lactate. The ingredients were side sweep at medium speed. A side phase containing Citric Acid and 10% of total water at room temperature was mixed together, and then added to the main kettle. The mixture was side sweep at medium speed. The rheology modifier was added to the main kettle and homogenized at medium speed. The mixture was homogenized for 10 minutes, then the temperature is reduced to 25 C. Once the temperature of 25 C was reached, the kaolin was added, as well as the filler, and a vegetal extract. The mixture was side sweep at medium speed. The sodium methyl cocoyl taurate was added and side sweep at medium speed. The betaine was added and side sweep at medium speed. Another polymer was added and mix at medium speed for 10 minutes. The viscosity and the pH was then adjusted.

Deposition of Salicylic Acid

A study of the deposition of salicylic acid was done on a number of subjects in order to evaluate the inventive formulas. The study included a disk stripping procedure developed internally. The deposition of salicylic acid was measured on the skin after the use of the product. Several formulas containing different amount of kaolin 0%, 2%, 10%, 20%, and 30% were studied. The application amount was about 30 mg of product to the studied area. The results are represented in Table 2 below.

TABLE 2

Residual of Salicylic Acid

| Formulas | Comparative example 1 (0% Kaolin) | Inventive Example 1 (2% kaolin) | Comparative Example 2 (10% kaolin) | Comparative Example 3 (20% kaolin) | Comparative Example 4 (30% kaolin) |
|---|---|---|---|---|---|
| Average Total residual µg | 20.83 | 23.11 | 23.51 | 23.58 | 23.71 |
| Residual on skin µg/cm² | 2.96 | 3.27 | 3.33 | 3.34 | 3.35 |

The deposition of salicylic acid observed for the formula containing no kaolin (comparative example 1) is 20.83. The formulas containing kaolin exhibit a higher salicylic deposition and the numbers are between 23.11 and 23.71. Therefore, it appears that the deposition of salicylic acid increases when kaolin is added to the formulas. The difference in deposition, µg/cm2, between the formula containing no kaolin and the formula containing 2% kaolin is about 10.5%.

The addition of kaolin into formulations thus surprisingly improved the deposition of salicylic acid. The inventive formula with 2% of kaolin has deposition of salicylic acid comparable with formulations where the concentration of kaolin is 10%, 20%, and 30%.

Example 2: Zein Solubility Test

The purpose of the Zein Solubility Test is to investigate the irritation potential (harshness) of a surfactant-based product. A high percent Zein Score represents irritation and harshness. A low percent Zein Score represents mildness and lack of irritation. Zein is a yellow corn protein that is similar to the keratin present in skin. It has limited solubility in water and is denatured (solubilized) by surfactants. The ability of surfactants to denature and solubilize zein has been linked to a surfactant's skin-irritation potential. The soluble zein protein is determined by utilizing a standard protein assay which measures protein absorbance values using a spectrophotometer. The amount of absorption correlates with the harshness of the product. The samples were tested and the results reported relative to a 1.5% solution of sodium laureate sulfate (SLS), as a positive control. The Zein Scores are expressed in terms of percentage of the SLS Zein Score. The measured mildness (% Zein) of the inventive and comparative are presented in Table 3 below.

The mildness of the Inventive Examples is significantly better than the comparative examples containing 20% or more of kaolin. The inventive examples 1 and 2 have a % Zein of 1.46% and 1.53% respectively, very close to the positive control (1.5%), meaning that both of them are very mild. Comparative example 2 exhibits a % Zein a little bit bigger (4.45%), meaning the formula with 10% of kaolin is not as mild as inventive examples 1 and 2. Comparative Examples 3 and 4 exhibit a number 10 times bigger than inventive examples 1 and 2. The numbers are ranging from 10.11% through 10.44%. The Comparative example 1 containing no kaolin does also have a small % Zein number, but as shown previously, does not have a good deposition of salicylic acid (20.83). On the contrary, the inventive example 1 does exhibit a good salicylic deposition (23.11)

Example 3: Evaluation of the Clay

Different types of clay were evaluated. The different clays were incorporated in formulas at a same percentage. The mildness and the salicylic deposition were measured and are presented in the Table 4 below.

TABLE 4

Evaluation of Different type of Clays

| Examples | Type of Clays | Zein % | Salicylic Acid Deposition Avg. Residual ug |
|---|---|---|---|
| Inventive example 2 | 2% Kaolin | 1.46% | 23.11 ug |
| Comparative example 5 | 2% Magnesium Aluminum Silicate | 1.10% | 20.7 ug |
| Comparative example 6 | 2% Moroccan Lava Clay | 1.74% | 15.91 ug |

From the results above, it is shown that the deposition of salicylic acid depends on the type of clay. The deposition of salicylic acid is equal to 23.11 ug in the case of the inventive example 1 containing 2% of kaolin. In the case of the comparative examples 5 and 6 containing 2% Magnesium Aluminum Silicate and 2% Moroccan Lava Clay, respectively, the deposition of salicylic acid is lower and equal to 20.7 ug in the formula containing 2% Magnesium Aluminum Silicate (comparative example 5) and 15.91 ug in the formula containing 2% Moroccan Lava Clay (comparative example 6).

Ratio of Clay and Surfactant

It was also demonstrated that the salicylic deposition as well as the mildness of the cleanser are dependent of the combination of a certain type of clay with a certain type of surfactant. The results are presented in Table 5 below.

TABLE 3

| Examples | Inventive Example 1 (2% kaolin) | Inventive Example 2 (2% kaolin) | Comparative Example 1 (0% kaolin) | Comparative Example 2 (10% kaolin) | Comparative Example 3 (20% kaolin) | Comparative Example 4 (30% kaolin) |
|---|---|---|---|---|---|---|
| % Zein | 1.53 | 1.46 | 1.14 | 4.45 | 10.11 | 10.44 |

TABLE 5

Comparison of salicylic acid deposition and Zein between formulas containing sulfate or taurate surfactants

| Examples | Name | Zein % | Salicylic Acid Deposition Avg. Residual ug |
|---|---|---|---|
| Inventive Example 2 | 3% of taurate with 2% Kaolin | 1.46% | 23.11 |
| Comparative Example 5 | 3% of taurate with 2% Magnesium Aluminum Silicate | 1.10% | 20.7 |
| Comparative Example 6 | 3% of taurate with 2% Moroccan Lava Clay | 1.74% | 15.91 |
| Comparative Example 7 | 3.75% of taurate with 30% Kaolin | 4.63% | 7.3 |
| Comparative Example 8 | 3.75% of taurate with 2% Magnesium Aluminum Silicate | 5.55% | 8.45 |
| Comparative Example 9 | 3.75% of taurate with 2% Moroccan Lava Clay | 3.7% | 8.27 |
| Comparative Example 10 | 3.8% of Sodium Laureth Sulfate with 2% Kaolin | 1.03% | 12.37 |

According to Table 5, it was demonstrated that a specific ratio between the kaolin and the taurate surfactant significantly improves the high deposition of salicylic acid as well as the mildness of the cleanser. The ratio between the taurate surfactant and the kaolin is crucial in order to observe a high deposition (see Inventive Example 2).

We also demonstrated that the type of sulfate is important if we want to observe a good salicylic acid deposition. In Comparative Example 10, the sulfate is a sodium laureth sulfate and even though the Zein % is very mild, the salicylic acid deposition is not in the range of the one observed with the inventive example.

The nature of the sulfate, as well as the ratio between the taurate sulfate and the kaolin is crucial in order to observe simultaneously the mildness and the salicylic acid deposition.

What is claimed is:

1. A cleanser composition comprising:
   a) from about 0.5% to about 20% of a taurate surfactant;
   b) from about 0.5% to about 2% of salicylic acid;
   c) from about 0.8% to about 4% of kaolin;
   d) from about 1% to about 15% of a betaine; and
   e) from about 0.5% to about 5% of an emollient selected from the group consisting of C12-15 alkyl lactate, C12-13 alkyl lactate and mixtures thereof;
   wherein all amounts are percentages by weight based on the total weight of the composition;
   wherein the composition is essentially free of sulfates.

2. The cleanser composition of claim 1, wherein the taurate surfactant is a compound selected from the group consisting of sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

3. The cleansing composition of claim 2, wherein the taurate surfactant is sodium methyl cocoyl taurate.

4. The cleanser composition of claim 1, wherein the salicylic acid is from about 0.8% to about 2% by weight based on the total weight of the composition.

5. The cleanser composition of claim 1, wherein the kaolin is from about 1% to about 4% of kaolin by weight based on the total weight of the composition.

6. The cleanser composition of claim 5, wherein the kaolin is from about 1.5% to about 4% of kaolin by weight based on the total weight of the composition.

7. The cleanser composition of claim 1, wherein the betain is selected from the group consisting of coco betaine, cocoamidopropyl betaine, lauryl betaine, laurylhydroxy sulfobetaine, lauryldimethyl betaine, cocoamidopropylhydroxylsulfo betaine, behenyl betaine, capryl/capramidopropyl betaine, lauryl hydroxysultaine, and stearyl betaine.

8. The cleanser composition of claim 7, wherein the betaine is coco betaine.

9. The cleanser composition of claim 1, wherein the emollient is C12-15 alkyl lactate.

10. The cleanser composition of claim 1, further comprising:
    f) A rheology modifier.

11. The cleanser composition of claim 10, wherein the rheology modifier is ammonium polyacryloyldimethyl taurate.

12. A cleanser composition comprising:
    a) from about 1.5% to about 15% of a taurate surfactant;
    b) from about 0.5% to about 2% of salicylic acid;
    c) from about 0.8% to about 4% of kaolin;
    d) from about 3% to about 10% of a betaine;
    e) from about 0.5% to about 5% of an emollient selected from the group of group consisting of C12-15 alkyl lactate, C12-13 alkyl lactate and mixtures thereof;
    f) from about 0.5% to about 2.5% of polymer selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer and
    wherein all amounts are percentages by weight based on the total weight of the composition;
    wherein the composition is essentially free of sulfates.

13. A method for cleansing the skin comprising applying the cleanser composition of claim 1 to the skin.

14. A method for cleansing the skin having make up comprising applying the cleanser composition of claim 1 to the skin.

15. The method for cleaning of claim 14, further comprising rinsing the skin.

* * * * *